July 21, 1942. C. A. CHASE Plant Pat. 532
ROSE PLANT
Filed Feb. 3, 1942
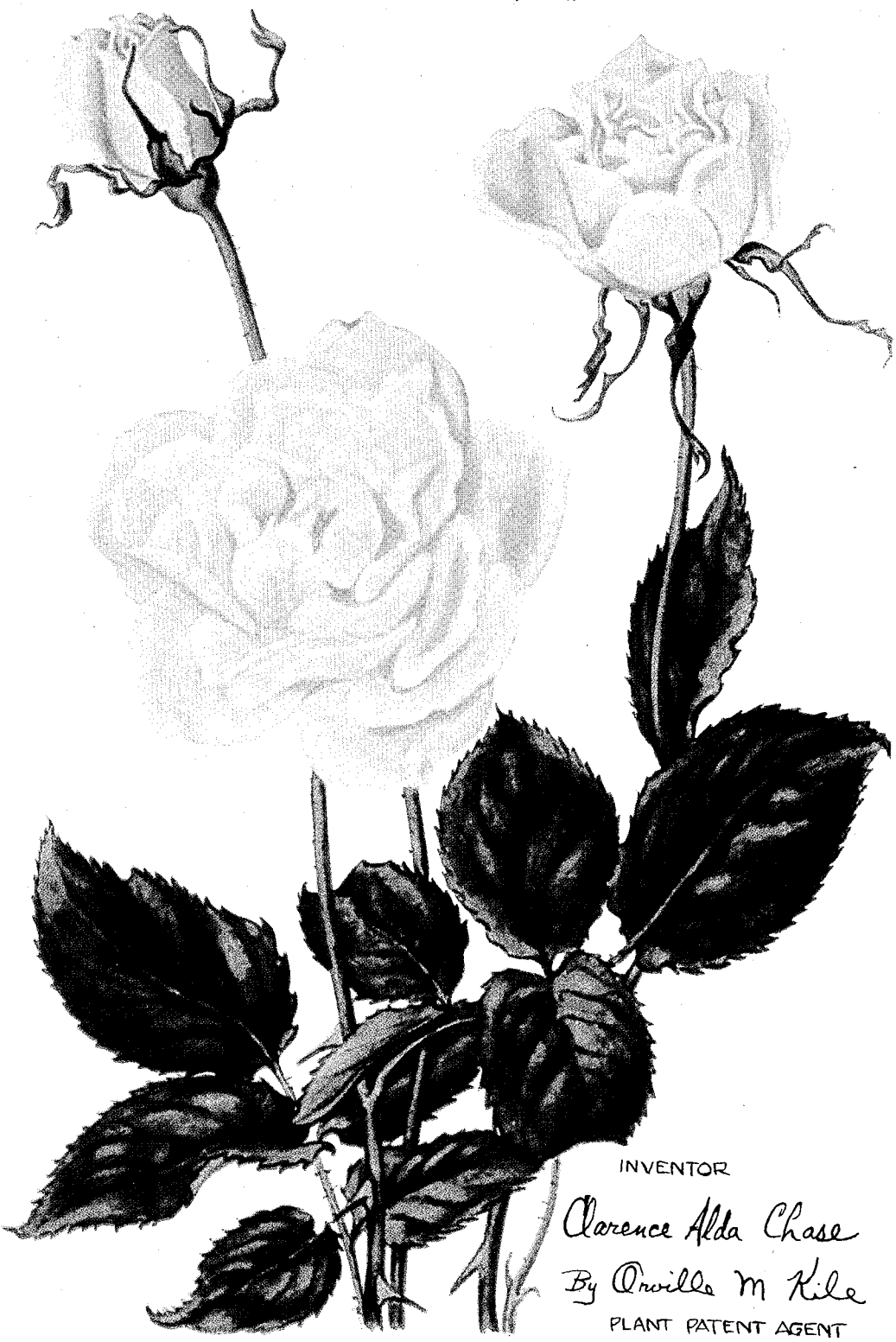
INVENTOR
Clarence Alda Chase
By Orville M Kile
PLANT PATENT AGENT Patented July 21, 1942

Plant Pat. 532

UNITED STATES PATENT OFFICE

532

ROSE PLANT

Clarence Alda Chase, Lane County, Oreg.

Application February 3, 1942, Serial No. 429,434

1 Claim. (Cl. 47—61)

My discovery relates to a new and improved variety of hybrid tea rose plants, with particular reference to growing habits and coloring of its flowers.

My new variety originated as a bud sport from the variety Talisman growing in my greenhouses and was discovered by me. A large stock of the variety has been built up by asexual reproduction and its characteristics have proved to be constant.

The growth of this new variety is exceptionally strong. The flower has an entirely different combination of coloring from that of its parent and the color is not affected by the sun. It is deeper in tone than most other roses in the same general class. It holds its color better than any other rose I have ever seen in this color range, this being a feature of prime commercial importance in roses of these general colors.

The form of the bud is more slender and graceful than that of other varieties of somewhat similar coloring.

The accompanying illustration which is a part of this application shows three specimens of the flower of this plant in different stages of opening, together with portions of the stems and leaves, as true to life as it was possible for the artist to show them. It must be understood that variations in coloring occur under varying conditions of growth.

In the following description of plant and flower, color plate designations refer to Ridgway's Color Standards and Nomenclature. However, no plates shown therein adequately describe the coloring of the blossom.

*The plant*

Growth habit: Upright bush; exceptionally vigorous and strong grower.

Blooming habit: Continuous and prolific producer of fine blooms borne singly on long stems.

Stems: Long; slender but strong; inclined to be staggered; Oil Green (Pl. V); beset with many thorns.

*Thorns.*—Many; very sharp and long; slightly downward-pointed; white or with pink tinge.

Foliage: Leaves compound, with 3 to 5 leaflets. Lateral leaflets are set close to rachis.

*Quantity.*—Very abundant.

*Color.*—Dark rich soft green. More nearly like Dark Cress Green (Pl. XXXI) than any other color shown by Ridgway, but much richer and brighter than that color plate.

*Size.*—Large terminal leaflet often measures 3 inches long by 1½ inches wide, sometimes more. Lateral leaflets on same stem measure very much less but in the same proportions.

*Shape.*—Leaflets elliptical with sharp point. Edge sharply and regularly serrate.

*Texture.*—Soft, leathery and smooth.

*Appearance.*—Glossy; brilliant; midrib deep, other veining indistinct.

*Rachis.*—Heavy; grooved above; several sharp thorns on under side.

*Stipules.*—Clinging; medium width and length; points long and very acute.

*The flower*

Bud:

*Size.*—Medium, measuring 1¾ to 2 inches in length just before opening.

*Form.*—Long, slender and very graceful rather than blunt or stubby as is usual with buds of the parent and others of this general color range.

*Color.*—Between Coral Red (Pl. XIII) and Scarlet (Pl. I). This is a wide range, however, and the true color cannot be adequately described by reference to standard guides known to me.

*Sepals.*—Long; inclined to be foliaceous; turn back early and cling against peduncle. Outer surface same color as peduncle; inner surface lighter and slightly fuzzy.

*Peduncle.*—Strong; very long; covered with spines; slightly lighter than stems in color.

*Calyx.*—Large; smooth; light green.

*Opening.*—Slow and perfect. Many of the opening buds display the unusual characteristic of partially opening, closing up to a tighter stage and then reopening. This procedure is sometimes repeated several times until the flower is fully opened. While this is a characteristic habit it is not always true.

Blossom:

*Size.*—Medium to large, averaging about 4½ inches in diameter.

*Form.*—Loose; high-centered. When in full bloom the row of five outer petals makes a frame which stands at right angles to the peduncle. The rest of the flower stands upright, holding its high center. Although the petalage is rather small, the rose looks very large, due primarily to the retention of its upright form and the wavy appearance of the petals in the mature flower. Stamens show only in the final stages of opening.

*Petalage.*—From 25 to 38 petals, according to season of year and vigor of particular flower shoot.

*Color.*—The general color effect is a richly glowing Capucine Yellow (Pl. III), surrounded by an outer row of petals of approximately Light Jasper Red (Pl. XIII). There is a distinctive glow over all, particularly on the inside of the petals. As the blossom opens it appears much lighter in color but this is due principally to the fact that more of the light inner surface of the petals is then visible. The color of this rose fades very little from exposure to the sun, this being a very excellent commercial characteristic.

Upon examination, it is found that the inner petals are Orange-Buff (Pl. III), slightly suffused with Light Coral Red (Pl. XIII) on the inner surface and almost completely covered by the latter color on the outer surface. The outer row of petals is approximately the same color on their inner surface as the outer surface of the remaining petals, and are a darker shade on their outer surface, approaching Jasper Red (Pl. XIII). In the final stages before wilting, the inner surface of the flower appears almost a golden yellow while the outer surface is between Carnelian Red (Pl. XIV) and Jasper Red (Pl. XIII), and the distinctive glow and sheen have largely disappeared. A very distinct aiglet of brilliant yellow is visible on both surfaces of the petals in all stages, although this is not so large as is often the case in blossoms of this general color range.

*Longevity.*—Lasts exceptionally well, particularly as a cut flower.

*Fragrance.*—Mild and very pleasing.

*Petals.*—*Size*—outer petals 1½ to 1¾ inches by 1¾ to 2 inches, the larger measurement being the perpendicular. *Shape*—outer petals almost round, with characteristic Talisman notch at the top. When the flower opens, the petals roll back very slightly and the inner petals are wavy on the edges. *Persistence*—cling until dead. *Texture*—substantial; velvety.

Reproductive organs:

*Pistils.*—Many; bunched. *Styles*—red; short. *Stigmas*—white.

*Stamens.*—Many, surrounding pistils and making a compact bunch. *Filaments*—short; deep yellow with occasional pink tinge. *Anthers.*—Light Cadmium (Pl. IV), edged with Cadmium Yellow (Pl. III).

*Comparison with Talisman*

The principal differences between this new variety and Talisman lie in the color of blossom and shape of bud.

1. Color of the parent flower is a combination of yellow, copper and reds in varigated form but the blossom of my new rose is a rich velvety orange or flame color evenly diffused over the inside surface, with slightly darker outer surface. Furthermore, the blossom of my variety has a distinctive glow, particularly on the inside of the petals.

2. The bud of my variety is long, slender and graceful, rather than blunt and short as that of its parent variety.

*Comparison with Cavalier*

Cavalier, the subject of Plant Patent No. 402, is more like my new variety than any other rose variety known to me, but it differs greatly in several respects, some of which are as follows:

1. The bud of my new variety is more shapely and graceful.

2. My variety is a sport of Talisman while Cavalier is a sport of Mrs. F. D. Roosevelt.

3. The yellow aiglet on the petals of my rose is not nearly so large or so pronounced, and the yellow line so frequently found up the middle of the petals of Cavalier rarely appears in my variety.

4. The petals of the open rose of my variety have a wavy appearance and are arranged more loosely than those of Cavalier, which characteristics help to give the effect of a large rose even with relatively small petalage.

5. The sepals of my variety turn back early, while those of Cavalier do not turn back to peduncle but remain almost at right angles. This gives an entirely different effect of the flower as a whole.

6. Stamens are tightly bunched in my new rose and loosely bunched in Cavalier.

7. My rose has a distinctive glow or sheen which is absent from Cavalier.

Having thus disclosed my discovery, I claim:

The new and distinct variety of rose plant herein shown and described, characterized particularly by its strong and vigorous growth; its long, shapely bud; the distinctive color, glow and sheen of its flowers; the lack of tendency of its flowers to fade in the sun; the slight waviness and loose formation of the petals in the open flower and the retention of the distinctive high-centered form; the many tightly bunched stamens; and the unusual trait of many of the newly-opened flowers of partially closing and later reopening.

CLARENCE ALDA CHASE.